(12) United States Patent
Belair

(10) Patent No.: US 6,588,916 B2
(45) Date of Patent: Jul. 8, 2003

(54) PAINT BOOTH LIGHTING FIXTURE

(75) Inventor: Guy Belair, Zanesfield, OH (US)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 63 days.

(21) Appl. No.: 09/939,935

(22) Filed: Aug. 27, 2001

(65) Prior Publication Data

US 2003/0039116 A1 Feb. 27, 2003

(51) Int. Cl.$^7$ .................................................. F21S 8/00
(52) U.S. Cl. ........................ 362/145; 362/253; 362/282; 362/238; 362/239; 362/241
(58) Field of Search ............................... 362/145, 253, 362/282, 238, 239, 241, 319, 147

(56) References Cited

U.S. PATENT DOCUMENTS

| | | |
|---|---|---|
| 3,829,677 A | 8/1974 | DeLlano |
| 4,242,725 A | 12/1980 | Douma et al. |
| 4,336,576 A | 6/1982 | Crabtree |
| 4,388,675 A | 6/1983 | Lewin |
| 4,598,344 A | 7/1986 | Nadler |
| 4,599,684 A | 7/1986 | Lee |
| 4,849,864 A | 7/1989 | Forrest |
| 4,924,365 A | 5/1990 | Bogdanovs |
| 5,426,575 A * | 6/1995 | Richards ..................... 362/283 |
| 5,510,965 A | 4/1996 | Teakell |
| 5,855,427 A * | 1/1999 | Lassovsky .................. 362/283 |
| 6,206,548 B1 * | 3/2001 | Lassovsky .................. 362/283 |
| 6,517,216 B1 * | 2/2003 | Cercone et al. ............. 362/220 |

* cited by examiner

Primary Examiner—Sandra O'Shea
Assistant Examiner—Ronald E. Delgizzi
(74) Attorney, Agent, or Firm—Rankin, Hill, Porter & Clark LLP; Alan T. McDonald; Vincent Ciamacco

(57) ABSTRACT

A paint booth lighting fixture having a sealed enclosure that receives a plurality of light bulbs, each of the bulbs having an individually adjustable reflector movably secured adjacent thereto. The reflectors are movable to direct light in a desired direction. The reflectors are held in a desired position and include an elongated body defining a series of elongated reflective surfaces.

22 Claims, 5 Drawing Sheets

PAINT BOOTH LIGHTING FIXTURE

BACKGROUND OF THE INVENTION

1. Field of the Invention

The present invention is generally directed toward lighting fixtures and, more particularly, toward lighting fixtures adapted for to provide optimal lighting in challenging environments.

2. Description of Related Art

Lighting in manufacturing and assembly applications is critical for a satisfactory result. Unfortunately, proper lighting is often difficult to attain due to the surrounding environment and the manufacturing process. For example, the lighting in paint booths in which automobiles are placed to correct minor cosmetic defects in the original paint or clear coat, is most often inadequate. Inadequate lighting makes it difficult for the painter to clearly see the area being painted, especially when the area being painted lies on the lower portion of the automobile.

In automobile manufacturing it is important to maintain acceptable standards for the facility and fixtures throughout the process. One of these established standards is that electrical lighting fixtures meet or exceed the requirements set forth by the Underwriters Laboratory (hereinafter referred to as UL requirements). For paint booth applications the UL requirements are quite rigid, and may have resulted in light fixtures meeting UL requirements at the expense of lighting effectiveness.

Typically, paint booth light fixtures are available as either rear access fixtures or front access fixtures, each having their own particular UL requirements. As the name would imply, rear access light fixtures are built into walls and are accessible for maintenance and repair only from the rear. As such, the light fixture has a frame incorporating a front wall in which a lens of the light fixture is sealably and immovably secured to the fixture frame. Rear access fixtures suffer from the disadvantage that they are inconvenient and expensive to install, and require rear access for maintenance, which may not be available in all installations.

On the other hand, front access light fixtures are also received within a wall recess, but have a pivotally mounted front door to gain access to the interior of the light fixture for maintenance and repair. Front access light fixtures are much more convenient for maintenance and repair, but need to have a reliable means of sealing the pivotal door to the fixture frame. Sealing is important not only to keep the paint particles from entering the interior of the fixture, but also to keep moisture, such as when the booth is being cleaned, from entering the fixture. Moreover, even with such front access light fixtures it is sometimes difficult to gain access to the interior of the fixture, especially when the door is hinged at its top edge to the frame.

As shown in FIG. 1, in conventional automobile paint booths, two rows of light fixtures are provided on each side of the automobile. The individual light fixtures are received in walls of the paint booth, and may be front access or rear access light fixtures, or a combination of front and rear access light fixtures. One row 10 of light fixtures is at the top of the wall and the other row 12 is at the bottom of the wall. In automobile paint booths, especially in paint booths wherein paint imperfections are to be corrected, consistent, even, and bright lighting is necessary. This is especially important on the lower portions of the car wherein visualization of the automobile surface is difficult.

Unfortunately, in automobile paint booth lighting fixtures known in the art, the light emanates from the light fixtures essentially normal or perpendicular to the wall, as shown by the dashed arrows 14 in FIG. 1. As such, the light is directed toward an area of the paint booth that does not require illumination. This has led to the tendency to provide the paint booth with more light fixtures holding more powerful light bulbs. Although this may increase the total light in the paint booth, it does so at the expense of higher energy and maintenance costs. Moreover, just having more candle power in the booth does not necessarily mean that the automobile surfaces are easier to view and inspect. Rather, the increased light may lead to further shadows, and to difficult viewing caused by glare from the lights. Therefore, there exists a need in the art for an improved paint booth lighting arrangement and for an improved paint booth lighting fixture that more precisely directs light from the fixture to the area to be inspected. There also exists a need in the art for a lighting fixture that is more efficient in providing light to the areas of interest, and a paint booth lighting arrangement that is more energy efficient.

SUMMARY OF THE INVENTION

Therefore, it is an objective of the present invention to provide a paint booth lighting fixture that meets UL requirements while providing improved lighting effectiveness. It is a further objective of the invention to provide a lighting fixture having an adjustable reflector wherein the light output by the lighting fixture can be readily directionally adjusted to meet the requirements of specific applications.

In accordance with the present invention, a lighting fixture includes a frame, a door pivotally and sealably secured to the frame to define an enclosed space, a series of elongated light bulbs received within the enclosed space, and a plurality of reflectors that are rotatably secured to the frame. Each of the reflectors is associated with and disposed relatively rearwardly of one of the light bulbs.

In further accordance with the present invention, the frame includes a back wall, a pair of side walls, and upper and lower walls, and a front face to which the door is pivotally secured. Each of the reflectors has end walls and an elongated body extending between the end walls. The end walls are releasably and rotatably secured to the frame.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

A first embodiment of the light fixture and reflector according to the present invention is illustrated in FIGS.

Figure 1:
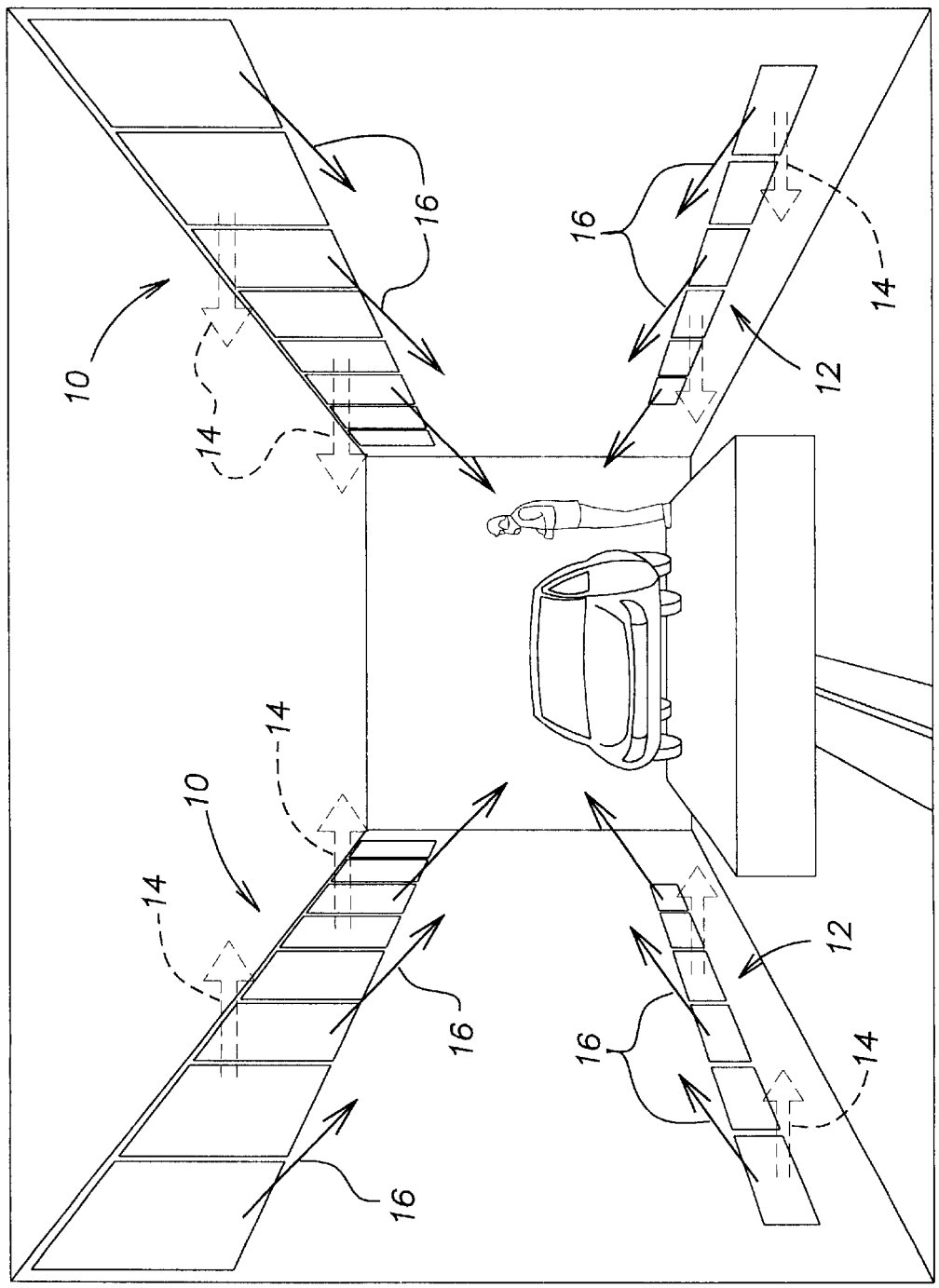
FIG. 1 illustrates a paint booth and the light pattern both with and without the reflectors according to the present invention.

2–5, wherein the fixture is shown to include a frame 20, a door 22 secured to a front of the frame 20, a series of elongated or tube-shaped light bulbs 24, and a series of elongated reflectors 26. The frame 20 includes a rear wall 28, an upper wall 30, a lower wall 32, a pair of side walls 34, and a front wall 36. The frame front wall 36 is preferably a rectangular mounting flange that extends outwardly from the upper, lower, and side walls 30, 32, 34 while defining a rectangular opening that is covered by the door 22, as will be described more fully hereinafter. Moreover, the frame 20 is adapted to be received within a wall of a paint booth such that the front wall or mounting flange 36 is adjacent a surface of the wall and substantially flush with the wall surface while the remainder of the frame 20 is received in a recess formed in the wall. This arrangement is generally illustrated in FIG. 1, wherein the light emitted from the light fixtures according to the present invention is shown by solid-line arrows 16.

Figure 4:
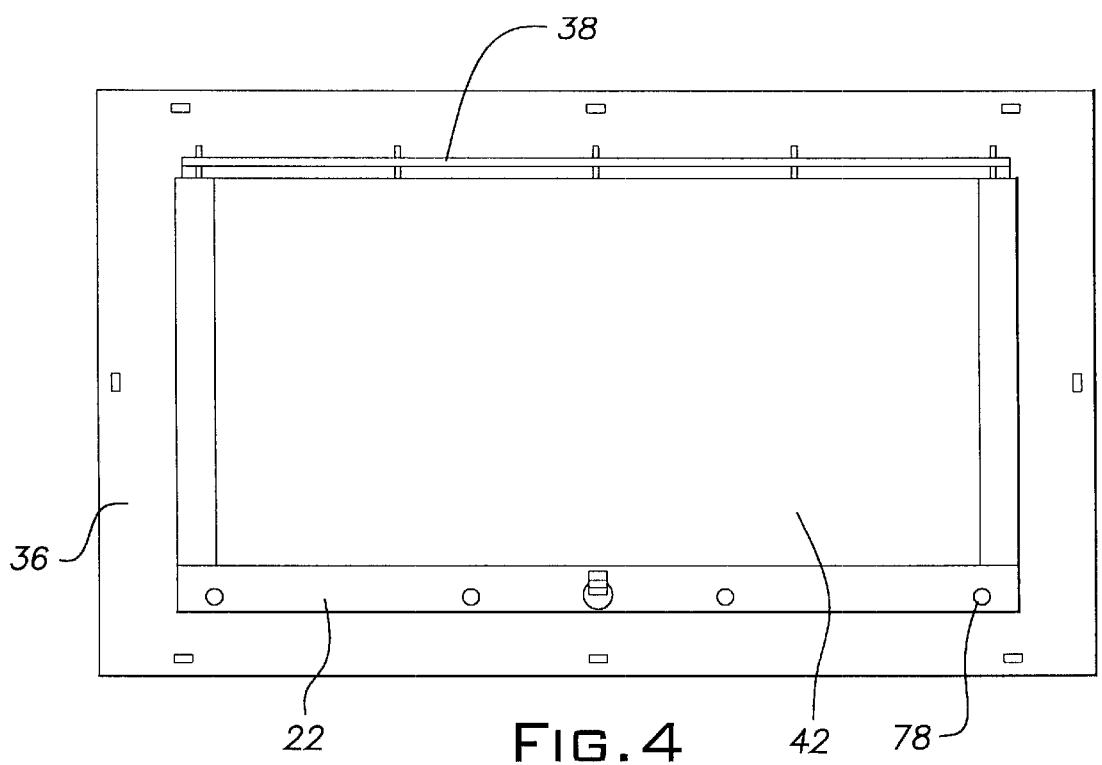
FIG. 4 is a front elevational view of the fixture of FIG. 2.
Figure 5:
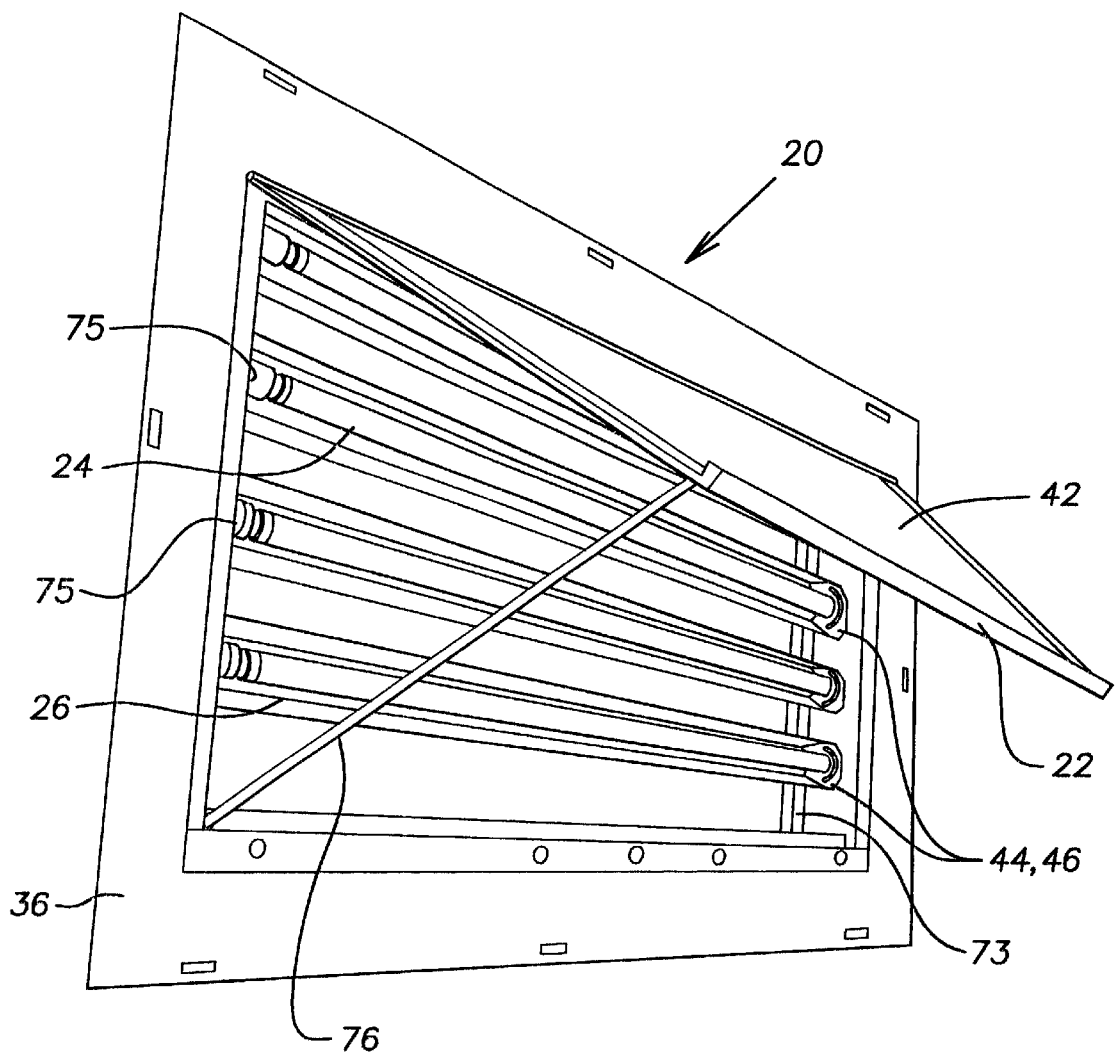
FIG. 5 is a perspective view illustrating a fixture with the door propped open.

The door 22 is pivotally or hingedly mounted to the frame 20 at the front wall 36 of the frame, preferably by means of a piano-type hinge 38 at the upper surface of the front wall, as shown in FIGS. 4–5. The door 22 and front wall 36 cooperate to provide a replaceable seal by means of which the pivotal door 22 is sealed to the frame 20. The replaceable seal may be an elastomeric ring-shaped seal 40 received within a corresponding groove formed in the front wall 36 of the frame 20 adjacent the opening therein. Alternatively, the groove may be formed at the periphery of the rearward-facing surface of the door 22. As such, the door cooperates with the frame to define an enclosure. The door is pivotally openable by means of the hinged connection 38 with the frame 20 to permit access to the interior of the fixture or enclosure. The door 22 defines a rectangular frame to which a lens or window 42 is sealably mounted. The lens or window 42 is preferably of tempered glass or similar suitable material.

Figure 7:
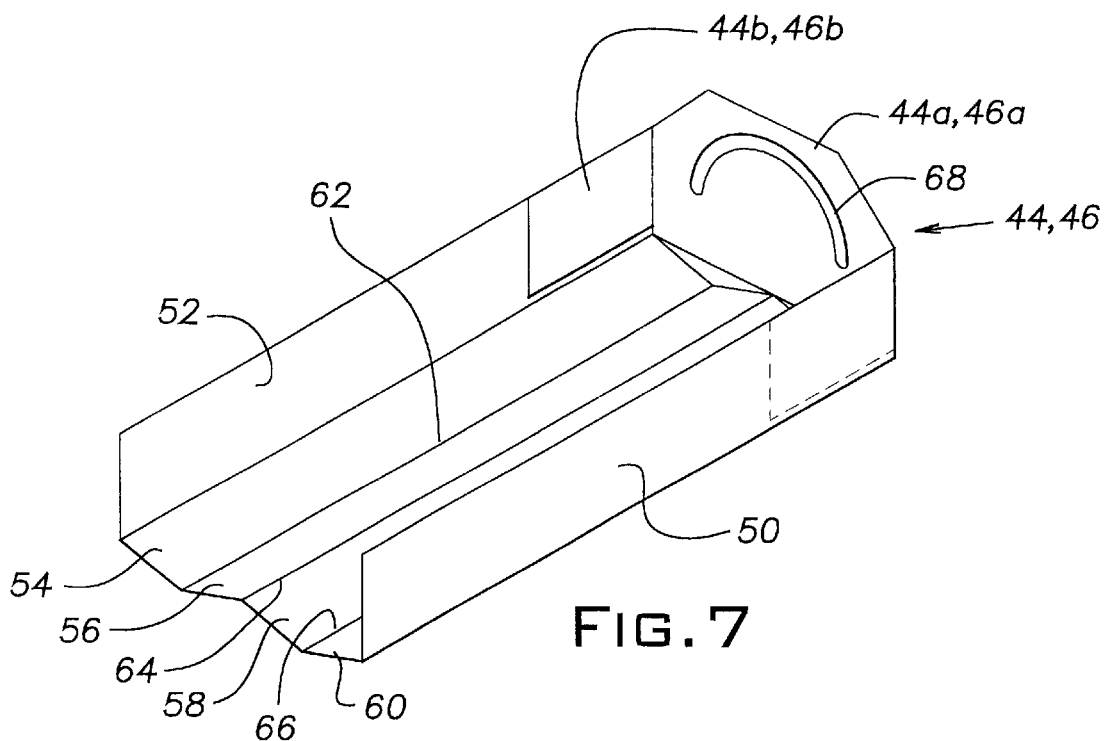
FIG. 7 is a partial perspective view showing an end of a reflector used in a front access fixture; and, FIG. 8 is a partial perspective view showing an end of a reflector used in a rear access fixture.

The reflectors 26 have identical first and second end caps 44, 46 and an elongated body 48 extending between the end caps 44, 46. The reflectors 26 are secured, by means of the end caps, to the fixture frame 20 and the lights 24 extend between the first and second end caps 44, 46. The elongated body 48 includes an upper wall 50, a lower wall 52, and a series of planar surfaces including first, second, third, and fourth elongated surfaces 54, 56, 58, 60. With reference to FIG. 7, the end caps 44, 46 include an end wall 44a, 46a and a pair of mounting ears 44b, 46b. The mounting ears 44b, 46b are secured to the upper and lower walls 50, 52 of the elongated body 48. The end wall 44a, 46a extends generally perpendicular to the length direction of the elongated body 48, as illustrated.

Figure 2:
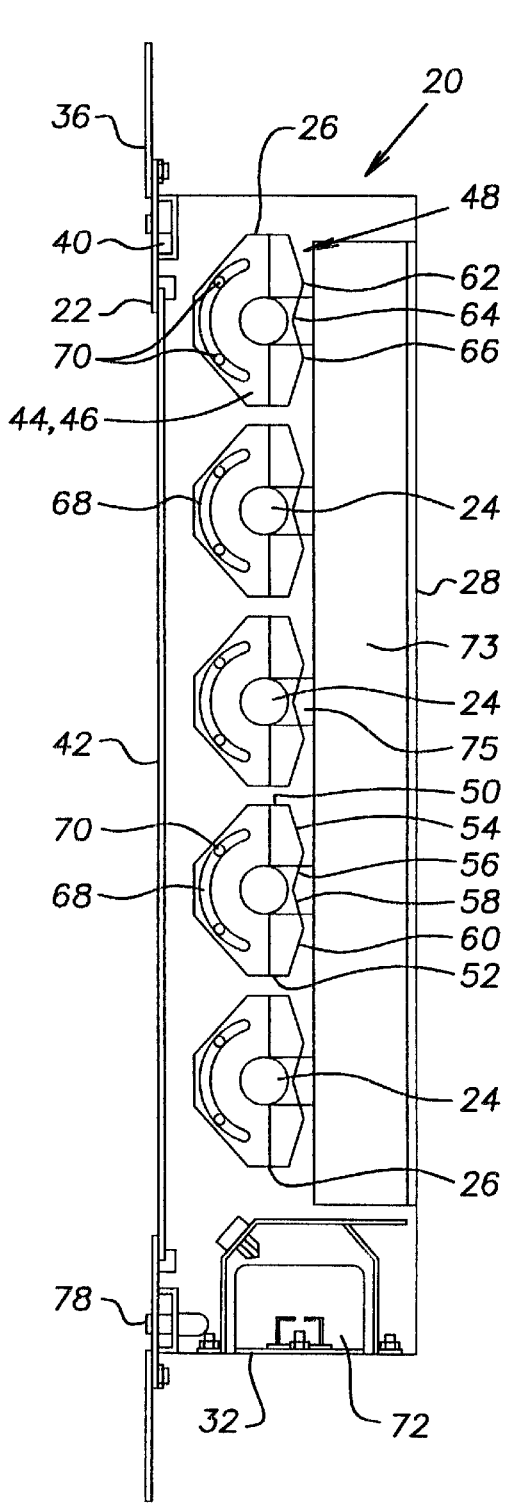
FIG. 2 is a schematic cross-sectional view of a front access light fixture according to the present invention.

As shown best in FIG. 2, which shows the reflectors 26 of a five-light, front access fixture in a neutral position (i.e., not tilted upwardly or downwardly relative to the light bulbs), the upper and lower walls 50, 52 of the reflector body 48 extends generally transverse or perpendicular to the axis of the light bulb 24. The first elongated surface 54 extends downwardly and rearwardly from the upper wall 50 of the reflector body 48 to the second elongated surface 56. Preferably, the angle between the upper wall 50 and the first elongated surface is between about 100–150 degrees and most preferably about 120 degrees. The intersection of the first and second elongated surfaces 54, 56 defines a valley or line 62 that is generally parallel to, but vertically above, the axis of the light bulb.

The second elongated surface 56 extends downwardly and forwardly from the first elongated surface 54 to the third elongated surface 58. Preferably, the angle between the first elongated surface 54 and the second elongated surface 56 is between about 100–150 degrees and most preferably about 120 degrees. The second and third elongated surfaces 56, 58 intersect at a vertical location that is generally equal to the vertical location of the axis of the light bulb and defines an elongated ridge or line 64 that is generally parallel to, but rearwardly spaced from, the light bulb axis.

The third elongated surface 58 extends downwardly and rearwardly from the second elongated surface 56 of the reflector body 48 to the fourth elongated surface 60. Preferably, the angle between the second elongated surface 56 and the third elongated surface 58 is between about 100–150 degrees and most preferably about 120 degrees. The intersection of the third and fourth elongated surfaces 58, 60 defines a valley or line 66 that is generally parallel to, but vertically below, the axis of the light bulb 24. The line 66 defined by the intersection of the third and fourth elongated surfaces 58, 60 is generally at a vertical distance from the light bulb axis that is equal to the vertical distance of the line 62 defined by the intersection of the first and second elongated surfaces 54, 56 from the light bulb axis. The fourth elongated surface 60 extends downwardly and forwardly from the third elongated surface 58 to the lower wall 52 of the reflector 26. Preferably, the angle between the third elongated surface 58 and the fourth elongated surface 60 is between about 100–150 degrees and most preferably about 120 degrees. Moreover, the angle between the fourth elongated surface 60 and the lower wall 52 is between about 100–150 degrees and most preferably about 120 degrees.

As shown best in FIGS. 2 and 7, each of the end walls 44a, 46a of the reflector end caps 44, 46 are shaped as a truncated triangle in which is formed a semi-circular slot 68. The slots 68 are adapted to receive reflector adjustment devices by means of which the reflectors 26 can be slidably and rotatably adjusted. Preferably, the reflector adjustment devices are screws 70 that are threadably received in openings formed in the fixture side walls 34. The screws 70 extend through the slots 68 such that the reflectors 26 can be slidably rotated to a desired orientation and, following tightening of the screws 70, be frictionally held in place without additional fasteners. Alternative easily adjustable fasteners, such as wing-nuts, may be threadably secured to posts extending from the side walls 34 and used to positively, yet releasably, secure the reflectors in the desired orientation. In this regard it is considered apparent that numerous equivalent means of securing the reflectors to the fixture frame are know in the art and may be used with equal functionality. By means of cooperation between the screws 70 and slots 68, the reflectors 26 may be angularly adjusted between about 20–40 degrees and more preferably about 30 degrees above and below the neutral position shown in FIG. 2.

Relatively beneath the lights, a ballast 72 is secured to the lower wall 32 of the fixture frame 20. Preferably, a ballast cover 74 is removably secured over the ballast 72. Placing the ballast 72 in this location makes it more readily accessible for removal and replacement, as is periodically necessary. A wire cover 73 is secured to each sidewall and serves to cover or contain wires extending from the ballast 72 to the light bulb sockets or holders 75. In the first embodiment, the end caps 44, 46 are secured to the side walls 34 at a location relatively forward of the wire cover 75.

Figure 3:
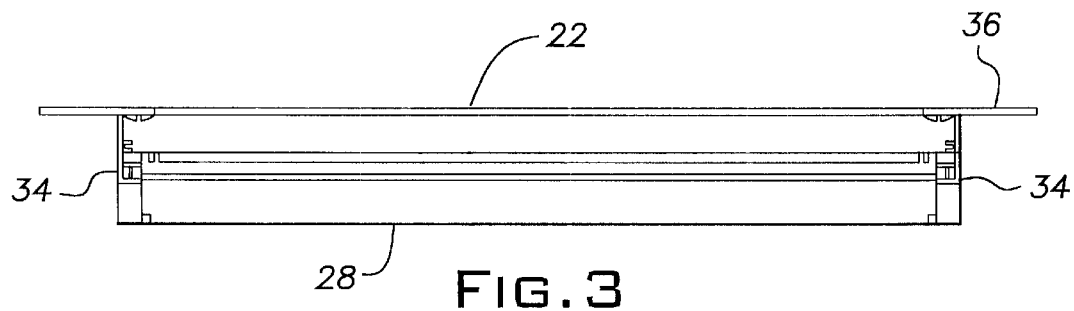
FIG. 3 is a top plan view of the fixture of FIG. 2.

In this regard, and with reference to FIG. 5, a four-lamp fixture, which is similar to the five lamp-fixture of FIGS. 2–4, is shown with the door 22 in an open position as would be the case for accessing the light bulbs 24 and ballast 72 for removal and replacement thereof. Also, the door 22 would be opened to adjust the reflectors 26 to the desired orientation to customize the light direction or output provided by the fixture. The fixture includes a prop rod 76 by means of which the door 22 can be maintained in an open position to facilitate access to the fixture interior. The prop rod 76 is preferably stored inside the light fixture. Preferably, the door 22 is secured, along its lower edge, to the fixture frame by means of a plurality of quick release fasteners 78, such as quarter turn spring loaded fasteners.

Figure 6:
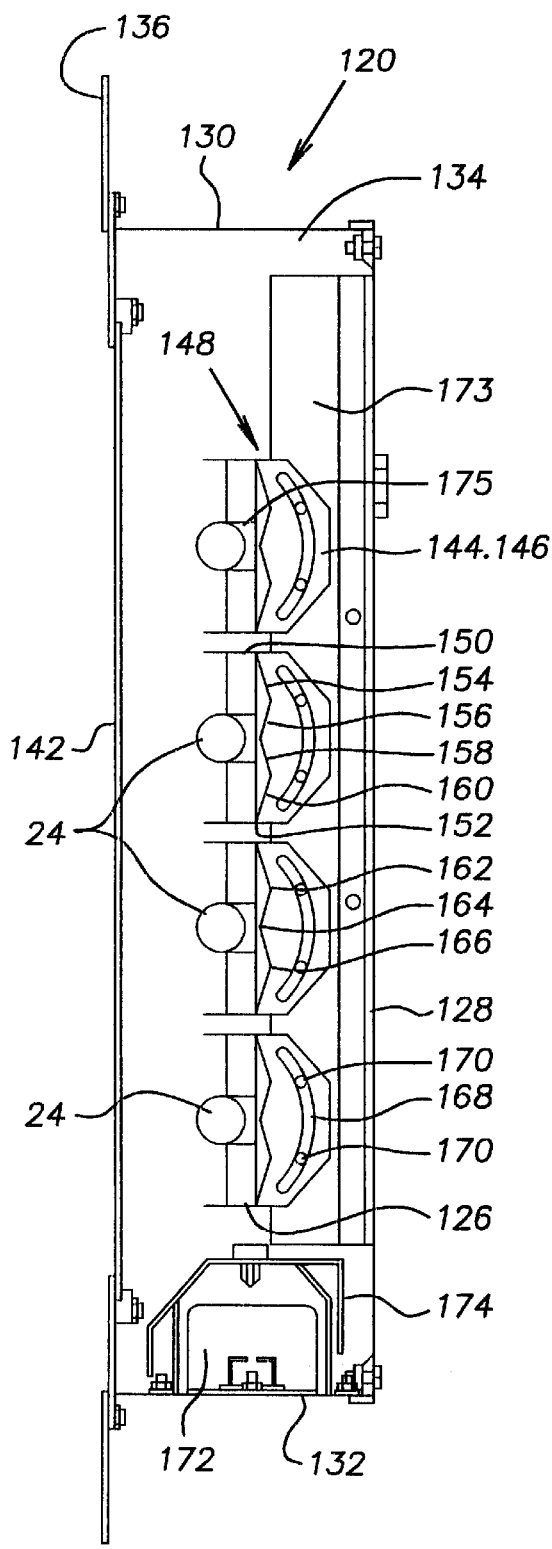
FIG. 6 is a schematic cross-sectional view of a rear access light fixture according to the present invention.

With reference to FIG. 6, a second embodiment of the paint booth light fixture, which is a four-light rear access fixture, is shown to include a rear wall 128, an upper wall 130, a lower wall 132, a pair of side walls 134, and a front wall or mounting flange 136 subtending an opening in which a lens 142 is secured. The rear wall 128 is removable to permit access to the interior of the fixture 120.

Within the fixture interior a plurality of light bulbs 124 and associated reflectors 126, which are shown in FIG. 6 in a neutral position, are installed. The reflectors 126 have identical first and second end caps 144, 146 and an elongated body 148 extending therebetween. The reflectors 126 are secured by means of the end caps 144, 146 to the fixture frame 120 and the lights 124 extend between the end caps. Similar to the first embodiment, the elongated reflector 126 of the second embodiment includes an upper elongated wall 150, an elongated lower wall 152 and a series of planar elongated surfaces including first, second, third, and fourth elongated surfaces 154, 156, 158, 160 extending between the first and second end caps 144, 146. The angular orientation of the surfaces 154, 156, 158, 160 is essentially identical to that described hereinbefore with reference to the elongated surface 54, 56, 68, and 60 of the first embodiment. The upper and lower elongated walls 150, 152 extend generally parallel to the associated light bulbs, when in the illustrated neutral position.

Figure 8:
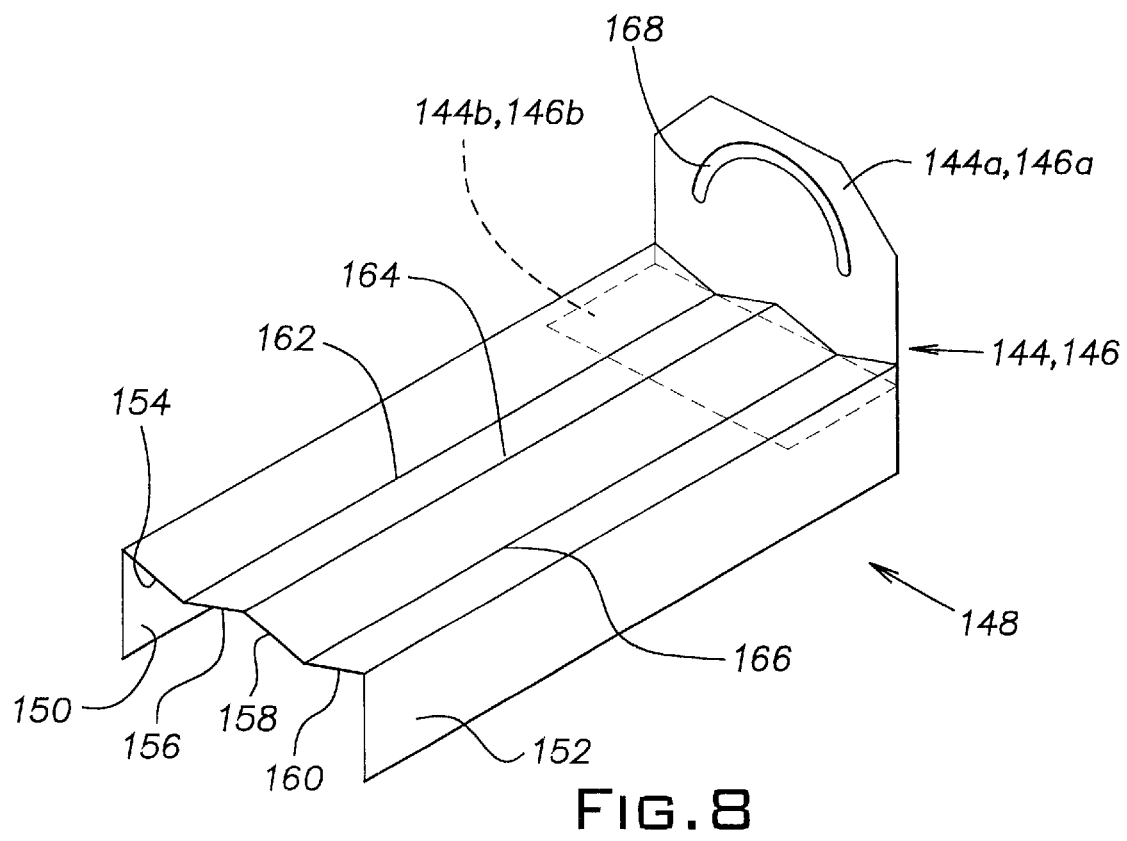

With reference to FIG. 8, the end caps 144, 146 include an end wall 144a, 146a and a transverse mounting flange 144b, 146b by means of which the end cap 144, 146 is secured to the reflector body 148. The mounting flange 144b, 146b is generally parallel to the length of the reflector 126, while the end wall extends transverse to the reflector length and generally rearwardly away from the reflector body 148, as will be apparent from the following discussion.

As shown best in FIG. 6, a width of the upper and lower walls 150, 152 of the reflector body 148 extends generally transverse or perpendicular to the axis of the light bulb 124. The first elongated surface 154 extends downwardly and rearwardly from the upper wall 150 of the reflector body 148 to the second elongated surface 156. The intersection of the first and second elongated surfaces 154, 156 define a valley or line 162 that is generally parallel to, but vertically above, the axis of the light bulb.

The second elongated surface 156 extends downwardly and forwardly from the first elongated surface 154 to the third elongated surface 158. The second and third elongated surfaces 156, 158 intersect at a vertical location that is generally equal to the vertical location of the axis of the light bulb 124 and defines an elongated ridge or line 164 that is generally parallel to, but rearwardly spaced from, the light bulb axis.

The third elongated surface 158 extends downwardly and rearwardly from the second elongated surface 156 of the reflector body 126 to the fourth elongated surface 160. The intersection of the third and fourth elongated surfaces 158, 160 define a valley or line 166 that is generally parallel to, but vertically below, the axis of the light bulb. The line 166 defined by the intersection of the third and fourth elongated surfaces 158, 160 is generally at a vertical distance from the light bulb axis that is equal to the vertical distance of the line 162 defined by the intersection of the first and second elongated surfaces 154, 156 from the light bulb axis. The fourth elongated surface 160 extends downwardly and forwardly from the third elongated surface 158 to the lower wall 152 of the reflector 126.

As shown best in FIGS. 6 and 8, the end wall 144a, 146a of the end caps extends opposite or away from the reflective surface of the reflector body 148. Each of the end walls 144a, 146a have a semi-circular slot 168 formed therein. The slots 168 are adapted to receive reflector adjustment devices by means of which the reflector 126 can be slidably adjusted. Preferably, the reflector adjustment devices are screws 170 that are threadably received in openings in the fixture side walls 134 or, in this embodiment, in the wire cover 173. The screws 170 extend through the slots 168 such that the reflectors can be slidably rotated to a desired orientation, and then frictionally held in place without additional fasteners. Alternative easily releasably fasteners, such as wing-nuts, may be threadably secured to posts extending from the side wall 134/wire cover 173, and used to positively, yet releasably, secure the reflectors 126 in the desired orientation. In this regard it is considered apparent that numerous equivalent means of securing the reflectors to the fixture frame are know in the art and may be used with equal functionality. By means of cooperation between the screws and slots, the reflectors may be angularly adjusted between about 20–40 degrees and more preferably about 30 degrees above and below the neutral position shown in FIG. 6.

Relatively beneath the lights, a ballast 172 is secured to the lower wall 132 of the fixture frame 120. Preferably, a ballast cover 174 is removably secured to over the ballast. Placing the ballast 172 in this location makes it more readily accessible for removal and replacement, as is periodically necessary. The wire cover 173 is secured to each sidewall and serves to cover wires extending from the ballast 172 to the lamp holder 175. The wire cover 173 also receives the reflector end cap adjustment screws 170, as described hereinbefore.

In practice, the re98flector 26, 126 is desirably adjusted such that light from the light bulb 24, 124, which would otherwise be lost within the fixture interior, is reflected in a direction useful to illuminating the automobile being inspected and/or painted. For example, the reflectors of fixtures in the upper row (FIG. 1) may be tilted or rotated downwardly (counter-clockwise in FIG. 2) while the reflectors of fixtures in the lower row may be tilted upwardly (clockwise in FIG. 2). Naturally, the reflectors may be individually adjusted or may be adjusted in common.

The present invention has been described herein with particularity, but it is noted that the scope of the invention is not limited thereto. Rather, the present invention is considered to be possible of numerous modifications, alterations, and combinations of parts and, therefore, is only defined by the claims appended hereto.

What is claimed is:

1. A paint booth lighting fixture comprising:
    a frame having a rear wall, an upper wall, a lower wall, a pair of side walls, and a front wall, said frame being adapted to be received within a structural wall such that said front wall is adjacent a surface of said structural wall and substantially parallel with said structural wall surface;

a door that is sealed to said frame and cooperates with said frame to define an enclosure, said door being pivotally openable to gain access to an interior of said enclosure;

a plurality of lights received within said enclosure;

a lens sealingly received in said door and through which light from said plurality of lights passes;

a plurality of movable reflectors, each of said plurality of light reflectors being disposed adjacent one of said plurality of lights and being operable to reflect light toward said lens, said reflectors being selectively and individually positionable so as to reflect light in a desired direction.

2. The paint booth lighting fixture according to claim 1, wherein each of said reflectors includes a pair of end caps and an elongated body extending between said end caps, said elongated body having a plurality of surfaces that are at angles to one another and are operable to reflect light from said adjacent light bulb through said lens.

3. The paint booth lighting fixture according to claim 2, wherein said elongated body further includes an upper wall and a lower wall and wherein plurality of surfaces include first, second, third and fourth surfaces.

4. The paint booth lighting fixture according to claim 3, wherein said first surface extends between said upper wall and said second surface, said second surface extends between said first surface and said third surface, said third surface extends between said second surface and said fourth surface, and said fourth surface extends between said third surface and said lower wall.

5. The paint booth lighting fixture according to claim 4, wherein an intersection between said first and second surfaces defines a first line that extends generally parallel to said light bulb.

6. The paint booth lighting fixture according to claim 5, wherein an intersection between said second and third surfaces defines a second line that extends generally parallel to said light bulb.

7. The paint booth lighting fixture according to claim 6, wherein an intersection between said third and fourth surfaces defines a third line that extends generally parallel to said light bulb.

8. A paint booth lighting fixture comprising:

a frame having a rear wall, an upper wall, a lower wall, a pair of side walls, and a front wall, said frame being adapted to be received within a structural wall such that said front wall is adjacent a surface of said structural wall and substantially parallel with said structural wall surface;

a lens sealingly received by said front wall;

a plurality of lights received within said enclosure;

a plurality of movable reflectors, each of said plurality of light reflectors being disposed adjacent one of said plurality of lights and being operable to reflect light toward said lens, said reflectors being selectively and individually positionable so as to reflect light in a desired direction.

9. The paint booth lighting fixture according to claim 8, wherein each of said reflectors includes a pair of end caps and an elongated body extending between said end caps, said elongated body having a plurality of surfaces that are at angles to one another and are operable to reflect light from said adjacent light bulb through said lens.

10. The paint booth lighting fixture according to claim 9, wherein said elongated body further includes an upper wall and a lower wall and wherein said plurality of surfaces include first, second, third and fourth surfaces.

11. The paint booth lighting fixture according to claim 10, wherein said first surface extends between said upper wall and said second surface, said second surface extends between said first surface and said third surface, said third surface extends between said second surface and said fourth surface, and said fourth surface extends between said third surface and said lower wall.

12. The paint booth lighting fixture according to claim 11, wherein an intersection between said first and second surfaces defines a first line that extends generally parallel to said light bulb.

13. The paint booth lighting fixture according to claim 12, wherein an intersection between said second and third surfaces defines a second line that extends generally parallel to said light bulb.

14. The paint booth lighting fixture according to claim 13, wherein an intersection between said third and fourth surfaces defines a third line that extends generally parallel to said light bulb.

15. An adjustable reflector for a paint booth lighting fixture, comprising:

a reflector body having a plurality of reflecting surfaces including an upper wall, a lower wall, and a series of elongated surfaces interconnecting said upper and lower walls, said plurality of elongated surfaces being at an angle to one another as well as to the upper and lower walls; and, first and second end caps secured to opposite ends of the reflector body, each of said end caps having an end wall that extends generally transverse to a length direction of said reflector body, said end caps including means for adjusting an angular orientation of said reflector.

16. The reflector according to claim 15, wherein said series of elongated surfaces include first, second, third and fourth surfaces, said first surface extending between said upper surface and said second surface, said second surface extending between said first and third surfaces, said third surface extending between said second surface and said fourth surface, and said fourth surface extending between said third surface and lower surface.

17. The reflector according to claim 16, wherein said upper and lower walls are generally parallel to one another.

18. The reflector according to claim 17, wherein the end wall extends in a relatively forwardly of said reflector body.

19. The reflector according to claim 17, wherein said end wall extends relatively rearwardly of said reflector body.

20. The reflector according to claim 16, wherein said end walls include slots through which fasteners extend to affix said reflector in a desired position.

21. The reflector according to claim 20, wherein the end wall extends in a relatively forwardly of said reflector body.

22. The reflector according to claim 20, wherein said end wall extends relatively rearwardly of said reflector body.

* * * * *